(12) United States Patent
Accinni

(10) Patent No.: US 11,951,117 B2
(45) Date of Patent: Apr. 9, 2024

(54) ANTIOXIDANT COMPOSITION COMPRISING POLYDATIN AND ACETYLCYSTEINE

(71) Applicant: SOLONGEVITY NUTRACEUTICALS S.r.l., Milan (IT)

(72) Inventor: Roberto Accinni, Milan (IT)

(73) Assignee: SOLONGEVITY NUTRACEUTICALS S.R.L., Milan (IT)

( * ) Notice: Subject to any disclaimer, the term of this patent is extended or adjusted under 35 U.S.C. 154(b) by 187 days.

(21) Appl. No.: 17/434,569

(22) PCT Filed: Feb. 21, 2020

(86) PCT No.: PCT/IB2020/051480
§ 371 (c)(1),
(2) Date: Aug. 27, 2021

(87) PCT Pub. No.: WO2020/174339
PCT Pub. Date: Sep. 3, 2020

(65) Prior Publication Data
US 2022/0117986 A1 Apr. 21, 2022

(30) Foreign Application Priority Data

Feb. 28, 2019 (IT) .................. 102019000002919

(51) Int. Cl.
| | | |
|---|---|---|
| *A61K 31/7034* | (2006.01) | |
| *A61K 31/194* | (2006.01) | |
| *A61K 31/198* | (2006.01) | |
| *A61K 33/04* | (2006.01) | |
| *A61P 39/06* | (2006.01) | |

(52) U.S. Cl.
CPC ........ *A61K 31/7034* (2013.01); *A61K 31/194* (2013.01); *A61K 31/198* (2013.01); *A61K 33/04* (2013.01); *A61P 39/06* (2018.01)

(58) Field of Classification Search
CPC .............. A61K 31/7034; A61K 31/194; A61K 31/198; A61K 33/04; A61P 39/06

USPC .......................................................... 514/35
See application file for complete search history.

(56) References Cited

U.S. PATENT DOCUMENTS

| | | |
|---|---|---|
| 2006/0264409 A1 | 11/2006 | Harty |
| 2007/0248690 A1* | 10/2007 | Trager ................ A61K 31/198 424/641 |
| 2009/0192227 A1 | 7/2009 | Tirouvanziam et al. |

FOREIGN PATENT DOCUMENTS

| | | |
|---|---|---|
| EP | 2 087 894 | 8/2009 |
| KR | 10-2011-0068258 | 6/2011 |
| WO | 00/64421 | 11/2000 |

OTHER PUBLICATIONS

Zhao et al. Polydatin prevents fructose-induced liver inflammation and lipid deposition through increasing miR-200a to regulate Keap1/Nrf2 pathway. Redox Biology 18 (2018) 124-137. (Year: 2018).*
Chen et al. Anti-oxidant polydatin (piceid) protects against substantia nigral motor degeneration in multiple rodent models of Parkinson's disease. Molecular Neurodegeneration 2015, 10:4, p. 1-14. Published: Mar. 2, 2015. (Year: 2015).*
Liu et al. The Antioxidative Function of Alpha-Ketoglutarate and Its Applications. BioMed Research International vol. 2018, Article ID 3408467, 6 pages. Published Mar. 21, 2018. https://doi.org/10.1155/2018/3408467 (Year: 2018).*
E. Esposito, et al., "A new co-micronized composite containing palmitoylethanolamide and polydatin shows superior oral efficacy compared to their association in a rat paw model of carrageenan-induced inflammation", European Journal of Pharmacology, ElSevier Science, vol. 782, Apr. 16, 2016, pp. 107-118 (12 pages).
Xinyi Zhao, et al., "Polydatin protects against carbon tetrachloride-induced liver fibrosis in mice", Archives of Biochemistry and Biophysics, Academic Press, vol. 629, Jun. 27, 2017, 7 pages.
International Search Report and Written Opinion of the ISA for PCT/IB2020/051480 dated Jun. 8, 2020, 12 pages.

* cited by examiner

*Primary Examiner* — Yih-Horng Shiao
(74) *Attorney, Agent, or Firm* — Nixon & Vanderhye, PC

(57) ABSTRACT

Antioxidant composition for increasing the levels of vitamins and reducing oxidative damage in a subject; the composition comprises an active agent, containing polydatin and acetylcysteine.

14 Claims, No Drawings

ANTIOXIDANT COMPOSITION COMPRISING POLYDATIN AND ACETYLCYSTEINE

This application is the U.S. national phase of International Application No. PCT/IB2020/051480 filed Feb. 21, 2020 which designated the U.S. and claims priority to IT Patent Application No. 102019000002919 filed Feb. 28, 2019, the entire contents of each of which are hereby incorporated by reference.

FIELD OF THE INVENTION

The present description refers to a composition particularly suitable for counteracting oxidative damage in a subject.

BACKGROUND OF THE INVENTION

The composition of the air in the atmosphere includes 21% of oxygen ($O_2$) by volume, an essential gas for life. Eighty percent or more of $O_2$ is used for the aerobic respiration process which allows efficient production of energy in the mitochondria of cells, in the form of adenosine 5'-triphosphate (ATP).

Some $O_2$ molecules are used by enzymes to catalyze essential reactions, which include the synthesis of the hormone adrenaline and the neurotransmitter dopamine, as well as the hydroxylation of amino acid residues during the formation of collagen, essential for the formation of connective tissues. The activity of the enzymes of the cytochrome P450 family also uses $O_2$ to metabolize xenobiotics, such as, for example, drugs, industrial chemicals, and toxins, transforming these compounds into less harmful products that are expelled from the human body.

Oxygen, however, although fundamental for metabolism, is a potentially toxic and mutagenic gas, and the human body has developed a wide range of antioxidant defenses that help to exercise a kind of protection against harmful effects. In addition to the antioxidants synthesized by the human body ("endogenous antioxidants"), the human diet can be enriched with antioxidants, mainly deriving from products of plant origin. Some plant-based antioxidants play an essential role (e.g. vitamin E and vitamin C). Others are not essential, but are nonetheless beneficial to human health (e.g. carotenoids and flavonoids).

In recent years, the use of antioxidants in the diet or consumed in a more concentrated form as additives and supplements has been the subject of numerous in vitro studies and experiments both in animals and in humans.

Glutathione, for example, is an endogenous antioxidant molecule capable of exercising an important activity in counteracting the physiological aging process. Glutathione is present in nature in all organisms, whether they are mono or multicellular. Its particular chemical structure makes this molecule particularly effective i) for counteracting the harmful action of free radicals formed as a natural by-product of normal oxygen metabolism and ii) for regulating cellular functions, such as, for example, synthesis and repair of DNA, protein synthesis, and the activation and regulation of enzymes important for the cellular metabolism of organisms.

Glutathione is also fundamental in cell detoxification processes, as it can perform the dual function of i) supporting the enzymes responsible for this action and ii) of binding toxins, transforming them into compounds that can be easily eliminated through bile and/or urine.

One of the known approaches to prevent or treat oxidative stress, for example, mediated by reactive oxygen species (ROS), can be based on the administration of antioxidants, such as glutathione, in order to stabilize or deactivate free radicals before they can damage healthy cells.

The bioavailability of glutathione in humans, however, is generally limited as the enzymatic systems of the digestive system, blood, and liver barrier degrade it quickly even when it is found in food in combination with other antioxidant compounds. Nutritional supplements based on glutathione undergo the same degradation processes and also the gastric, blood and liver barriers retain a large part; in fact, only a small part is able to reach the bloodstream to exert beneficial effects in the body.

Furthermore, glutathione levels decrease physiologically with the progress of age, with a consequent increase in cellular aging processes.

There are also exogenous factors capable of determining its reduction, such as environmental conditions (radiation, smog, and pollution); incorrect lifestyles (cigarette smoking, alcohol abuse); obesity (excess of fatty foods, which can increase the levels of oxidative stress).

Due to the factors listed above, administering nutritional compositions, including, for example, glutathione as an antioxidant, have not always proven to be effectively efficient in combating oxidative damage.

SUMMARY OF THE INVENTION

The object of the present description consists in providing a composition with a high antioxidant capacity, and capable of overcoming the drawbacks outlined above. The described composition causes a surprising increase in the plasma levels of vitamins A, E and C, and a decrease in the levels of neopterin (an inflammation marker).

According to the invention, the aforesaid object is achieved thanks to the subject specifically referred to in the following claims, which are intended as an integral part of the present description.

One embodiment of the present description provides an antioxidant composition comprising an active agent, the active agent containing polydatin and acetylcysteine.

In one or more embodiments, the active principle may comprise—in addition to polydatin and acetylcysteine—at least one additional component selected from the group consisting of glutamine, glycine, alanine, α-ketoglutaric acid, selenium (SE).

In one or more embodiments, the active agent of the composition comprises polydatin and acetylcysteine, in combination with α-ketoglutaric acid, glutamine, glycine, alanine and selenium (Se).

Glutamine and α-ketoglutaric acid can also be contained in the active principle in the form of glutamine α-ketoglutarate (glutamine akg). In one or more embodiments, the active agent of the composition comprises polydatin and acetylcysteine, in combination with glutamine α-ketoglutarate, glycine, alanine and selenium (Se).

The composition described herein may further comprise minerals, additives and flavoring substances.

An additional embodiment of the present description provides a method for treating oxidative stress in a subject, the method comprising selecting a composition comprising an active agent containing polydatin in combination with acetylcysteine and, optionally, with at least one additional component selected from the group consisting of glutamine, glycine, alanine, α-ketoglutaric acid, selenium, and administering the composition to the subject.

The disclosure also provides a method for treating at least one vitamin deficiency disease, the method comprising administering a therapeutically effective amount of the described composition to the subject. Vitamin deficiency diseases can be selected from nyctalopia, ataxia, cystic fibrosis, Crohn's disease, macular degeneration, and senile hearing loss.

In one or more embodiments, the compositions described herein can also be used in medicine. The compositions subject of the present description have proven effective in preventing and/or treating an inflammatory state, and for treating vitamin deficiency diseases such as nyctalopia, ataxia, cystic fibrosis, Crohn's disease, macular degeneration and senile hearing loss.

DETAILED DESCRIPTION OF THE INVENTION

In the following description, there are numerous specific details to provide a thorough understanding of the embodiments. The embodiments may be implemented in practice without one or more of the specific details, or with other methods, components, materials, etc. In other cases, well-known structures, materials or operations are not shown or described in detail to avoid obscuring certain aspects of the embodiments.

Reference throughout the present disclosure to "one embodiment" or "an embodiment" indicates that a particular aspect, structure or characteristic described with reference to the embodiment is included in at least one embodiment. Thus, forms of the expressions "in one embodiment" or "in an embodiment" at various points throughout the present description are not necessarily all referring to the same embodiment. Moreover, the particular aspects, structures or characteristics can be combined in any convenient way in one or more embodiments.

The titles provided in this description are for convenience only and do not interpret the scope or object of the embodiments.

One embodiment of the present description provides a composition comprising an active agent, said active agent comprising polydatin and acetylcysteine.

The weight ratio between polydatin and acetylcysteine can be between 0.10 and 0.50, preferably between 0.15 and 0.30.

The active principle of the composition may also comprise an additional component selected from the group consisting of glutamine, glycine, alanine, α-ketoglutaric acid and selenium (SE).

In another embodiment, glutamine and α-ketoglutaric acid can be contained in the active principle in the form of glutamine α-ketoglutarate. In this case, the active principle may contain—in combination with polydatin and acetylcysteine—at least one additional component selected from glutamine α-ketoglutarate, glycine, alanine and selenium.

The compositions of the present application have a high antioxidant capacity and can be used in preventing and/or treating an oxidative stress disease such as, for example, an acute or chronic inflammatory state. The compositions may also be intended for use in treating diseases caused by vitamin deficiencies, for example, selected from the group consisting of nyctalopia, ataxia, cystic fibrosis, Crohn's disease, macular degeneration and senile hearing loss.

Polydatin (also known as piceid) present in the active agent of the compositions described here is a natural molecule with antioxidant activity that can be extracted, for example, from the roots of a plant, *Poligonum cuspidatum*, originating from North East Asia.

Polydatin is able to interact with the epigenome by activating the synthesis of sirtuins, proteins which—in turn—trigger a series of positive reactions ranging from DNA repair, activation of Phase II enzymes (antioxidants), and activation of glutathione-peroxidase (GPX) and glutathione-S-transferase (GST).

The Inventors of the present application have demonstrated a surprising effect exerted by compositions in which polydatin is present in the active principle in combination with acetylcysteine and—optionally—with at least one additional component selected from the group consisting of glutamine, glycine, alanine, α-ketoglutaric acid and selenium (Se). In one or more embodiments, glutamine and α-ketoglutaric acid can be contained in the active principle in the form of glutamine α-ketoglutarate.

These compositions are particularly effective when the various components are present in the quantities indicated below.

Polydatin can be present in an amount less than 15% (weight/weight) of the active agent, preferably between 3% and 15% (weight/weight), more preferably equal to 5% (weight/weight) of the active agent.

Acetylcysteine can be present in an amount between 25% and 35% (weight/weight), preferably between 28% and 32% (weight/weight) of the active agent.

The weight ratio between polydatin and acetylcysteine can be between 0.10 and 0.50, preferably between 0.15 and 0.30.

Glutamine, when present in the active ingredient, can be contained in an amount between 10% and 20% (weight/weight), preferably between 12% and 18% (weight/weight) of the active agent.

α-ketoglutaric acid can be contained in an amount between 10% and 20% (weight/weight), preferably between 12% and 18% (weight/weight) of the active agent.

The amount of glycine can be between 10% and 18% (weight/weight), preferably between 12% and 16% (weight/weight) of the active agent.

Alanine can be present in an amount between 10% and 25% (weight/weight), preferably between 15% and 20% (weight/weight) of the active agent.

The amount of selenium contained in the composition can be between 0.01% and 0.03% (weight/weight) of the active agent.

When the active principle contains glutamine α-ketoglutarate (in addition or as an alternative to glutamine and α-ketoglutaric acid), this salt can be present in the composition in an amount comprised between 20% and 40% (weight/weight), preferably between 25% and 35% (weight/weight) of the active agent.

The compositions described may comprise at least one additional component selected from vitamins, minerals, additives and flavoring substances.

In one or more embodiments, the compositions subject of the present description can be administered as an oral nutritional supplement.

The Inventors have shown that the compositions subject of the present application allow significant acceleration of the cellular metabolism by simultaneously increasing the reduced species and decreasing the oxidized species, both in the plasma and in the erythrocytes. Furthermore, an even more surprising effect is observed on the synthesis of vitamins C, E and A, and on the reduced synthesis of neopterin (inflammation marker), as will be evident below.

Examples

Table 1 presents non-limiting illustrative examples of compositions (A, B, C) according to embodiments of the present description.

TABLE 1

|  | Comp. A mg (mmol) | Comp. B mg (mmol) | Comp. C mg (mmol) |
| --- | --- | --- | --- |
| Glutamine α-ketoglutarate (Glutamine akg) | 45(0.14) | 217(0.7) | 525(1.8) |
| N-acetylcysteine | 45(0.28) | 210(1.4) | 600(3.6) |
| Glycine | 21(0.28) | 105(1.4) | 270(3.6) |
| Alanine | 25(0.28) | 126(1.4) | 320(3.6) |
| Polydatin | 20(0.05) | 35(0.09) | 200(0.5) |
| Selenium | 0.035(0.0004) | 0.15(0.0016) | 0.25(0.0028) |
| Total (mg) | 156.035 mg | 693.15 mg | 1915.25 mg |

The compositions can be prepared as follows. The components (purchased from the company Solimè S.r.l., Cavriago, Reggio Emilia, Italy), which have been previously selected and weighed, are inserted in sequence into a carefully sanitized paddle mixer (A091). In particular, glutamine akg, n-acetylcysteine, alanine, glycine, polydatin and sodium selenite are mixed thoroughly for at least 10 minutes. Consequently, the mixing is suspended and observed in order to verify the obtainment of a perfectly homogeneous product. Mixing can resume for an additional 10 minutes. When mixing is complete, the entire batch is poured into one or more disposable polyethylene bags, in quantities not exceeding 10 kg per bag. A sample of the product is taken and subjected to organoleptic control for appearance/shape, color, odor and microbiological control for total bacterial count (TBC), yeasts and molds. The product is transferred to a dedicated area (zone 34) pending analytical reports. Downstream of the positive results of the analyzes carried out, the mixture is subjected to encapsulation with an automatic encapsulator (A029) at maximum speed 4 (equal to 20,000 cps/h), at the rate of 350 mg of active compounds per gelatin capsule (zero format, 90 mg) for a total weight of 440 mg each. At the end of the processing, the product is transferred to an area dedicated to packaging (zone 12) for the blister and cartoning phases.

Table 2 shows two different compositions that have been the subject of clinical trials.

The composition called "HOPE A" comprises an active agent containing polydatin, N-acetylcysteine, glutamine α-ketoglutarate, glycine, alanine and selenium.

The composition called "HOPE B" differs from the composition "HOPE A" in that it does not contain polydatin.

TABLE 2

| Components | HOPE A (mg) | HOPE B (mg) |
| --- | --- | --- |
| Glutamine α-ketoglutarate | 217 | 217 |
| N-acetylcysteine | 210 | 210 |
| Glycine | 105 | 105 |
| Alanine | 126 | 126 |
| Polydatin | 35 | — |
| Selenium | 0.15 | 0.15 |

Materials and Methods

A total of 30 healthy, asymptomatic volunteers of both sexes aged between 45 and 75 were selected. All subjects selected for the study signed informed consent. Subjects who met the following exclusion criteria did not participate in the study:
Pregnant women;
Subjects who regularly took drugs that inhibit homocysteine metabolism (methotrexate, anti-epileptics, etc.);
Pathology carriers;
Subjects subjected to therapies with chemotherapy.

Study participants were divided into two groups: A and B, each group comprising 15 volunteers.

Each participant, following a medical examination to evaluate their suitability, had blood, urine and saliva samples taken.

The subjects of group A (consisting of 7 males and females, average age: 59±12 years) were given the HOPE A composition in the form of 140 capsules. The capsules were taken daily in the dosage of 2 capsules per day, on a full stomach (after a meal).

The subjects of group B (consisting of 7 males and females, average age: 60±10 years) were given the HOPE B composition in the form of 140 capsules. The capsules were taken daily in the dosage of 2 capsules per day, on a full stomach (after a meal).

After the first 8 weeks, at the end of the experiment, a second blood sample was taken, along with urine and saliva collection. The participants continued to take the drugs prescribed to them by the attending physicians, and were instructed to report any pathological states that occurred during the trial period, the drugs taken for this purpose and any changes in lifestyle and in particular changes in eating habits.

In the biological samples (blood, urine and saliva) taken from each of the 30 volunteers, the following parameters were analyzed at baseline sampling (time 0, t0) and after 8 weeks (t1): Cysteine, Homocysteine, Cysteinylglycine, and Glutathione in oxidized and reduced forms, in plasma, erythrocytes and saliva. In the blood, vitamin C, vitamin E and vitamin A levels were evaluated. In the urine, neopterin was quantified as an inflammatory marker. In the serum, Transaminase (ALT, AST, GGT), Total Cholesterol, HDL, LDL, Triglycerides, Reactive Protein C (PCR), and Glycaemia were evaluated.

Analysis Procedures

1) HPLC Determination of Urinary Neopterin Levels

The analysis was carried out at the Clinical Biochemistry Laboratory of the Clinical Physiology Institute of the CNR in Milan. The dosage of urinary neopterin, normalized for urinary creatinine analyzed in the same sample using two detectors in series, was performed with the HPLC method: the urine sample after being diluted with the mobile phase, was injected into an isocratic HPLC system with a reverse phase column and UV detector (for Creatinine dosage) and spectrofluorimetric detector (for neopterin dosage); the chromatographic peaks of creatinine and neopterin were integrated by dedicated software and their concentration determined by means of calibration curves.

2) HPLC Determination of the Plasma and Erythrocyte Levels of the Main Circulating Thiols The analysis was carried out at the Clinical Biochemistry Laboratory of the Clinical Physiology Institute of the CNR in Milan.

Total and reduced aminothiols were measured in erythrocytes and plasma according to a method previously validated and described in Dellanoce, C.; Cozzi, L.; Zuddas, S.; Pratali, L.; Accinni, R. Determination of different forms of aminothiols in red blood cells without washing erythrocytes. Biom. Chrom. 28(3): 327-331; 2014.

Briefly, Tris-(2 carboxyethyl)-phosphine hydrochloride (TCEP) and 4-fluoro-7-sulfamoylbenzofurazan (ABD-F) were used, respectively, as reducing and derivatizing agents; the reduced aminothiols were evaluated by mixing erythrocytes and plasma with 10% trichloroacetic acid (1:1 v/v). 10 µL of 0.4 M NaOH, 70 µL of 1 M borate buffer at pH 11 containing 4 mM EDTA, 30 µL of 1 M borate buffer at pH 9.5 containing 4 mM EDTA and 10 µL 10 g·L-1 ABD-F in borate buffer (1M pH 9.5, containing 4 mM EDTA) were added to 100 µL of each supernatant obtained. Samples were incubated at 4° C. for 90 min and then 10 µL was injected into the HPLC system for analysis.

Separation of the thiols occurs at room temperature by high performance isocratic liquid chromatography on a Discovery C-18 column (250×4.6 mm in diameter, Supelco, Sigma-Aldrich), eluted with a 0.1 g solution, L-1 acetate buffer, pH 4.0: methanol, 81:19 (v/v), with a flow of 1 mL min$^{-1}$. The fluorescence intensity was measured with an excitation at 390 nm and emission at 510 nm, using a Jasco fluorescence spectrophotometer. Samples were measured by a standard calibration curve.

3) HPLC Determination of the Serum Levels of Vitamin A, Vitamin E, Vitamin C

The analysis was carried out at the Clinical Biochemistry Laboratory of the Clinical Physiology Institute of the CNR in Milan, using commercial kits (Chromsystem) with European certification.

Results

The biochemical parameters, after daily intake for weeks of the compositions HOPE A and HOPE B, are shown in Tables 3 and 4 below, where the average values are indicated (with standard deviations) and the percentage variation of the average levels of the values (Δ %) found at baseline sampling (t0) or before the start of the trial and after 2 months of treatment (t1).

TABLE 3

|  | HOPE A | | | HOPE B | | |
| --- | --- | --- | --- | --- | --- | --- |
|  | t0 | t1 | Δ% | t0 | t1 | Δ% |
| rp CYS | 14.3 ± 1.6 | 19.4 ± 6 | 39↑ | 17.4 ± 1.7 | 19.3 ± 2 | 11↑ |
| rp CYSGLY | 5.3 ± 1.8 | 8 ± 3.4 | 52↑ | 7.6 ± 2.2 | 9.5 ± 2 | 26↑ |
| op CYS | 300 ± 75.6 | 215.5 ± 41.8 | 26.7↓ | 292 ± 34 | 213 ± 39 | 25↓ |
| op CYSGLY | 77.5 ± 26 | 54.4 ± 12 | 26.5↓ | 75 ± 10 | 47 ± 10 | 36↓ |
| re CYS | 17.5 ± 2.2 | 13.7 ± 3.2 | 22.3↓ | 17.9 ± 1.7 | 14.5 ± 1.2 | 19↓ |
| re CYSGLY | 5.4 ± 1.8 | 7.1 ± 2.26 | 32.5↑ | 3.81 ± 0.5 | 4.7 ± 0.5 | 25↑ |
| re GSH | 967.6 ± 283 | 1350 ± 367 | 43↑ | 958.4 ± 123 | 1265 ± 145 | 32↑ |
| oe CYS | 28.4 ± 3 | 19.4 ± 4 | 31.5↓ | 27 ± 3 | 21.4 ± 4 | 22↓ |
| oe CYSGLY | 3.5 ± 0.8 | 2 ± 0.5 | 42↓ | 3.4 ± 0.7 | 2 ± 0.3 | 47↓ |
| oe GSH | 1262 ± 321 | 647 ± 271 | 49↓ | 1557 ± 1517 | 232 ± 197 | 78↓ |

List of abbreviations: reduced plasma cysteine (rp cys), reduced plasma cysteinylglycine (rp cysgly), oxidized plasma cysteine (op cys), oxidized plasma cysteinylglycine (op cysgly), reduced erythrocytic cysteine (re cys), reduced erythrocytic cysteinylglycine (re cysgly), reduced erythrocytic glutathione (re GSH), oxidized erythrocytic cysteine (oe cys), oxidized erythrocytic cysteinylglycine (oe cysgly), oxidized erythrocytic glutathione (oe GSH).

Table 4 below shows the values of Vitamins A, E, C and neopterin in the two groups of subjects. Also in this case, the average values (with standard deviations) and the percentage variation of the average levels of the values (Δ %) found at the basal sampling (t0) or before the start of the experimentation, and after 2 months of treatment (t1) are indicated.

TABLE 4

|  | HOPE A | | | HOPE B | | |
| --- | --- | --- | --- | --- | --- | --- |
|  | t0 | t1 | Δ% | t0 | t1 | Δ% |
| Vit. A | 36.9 ± 10 | 51 ± 10 | 47↑ | 49.7 ± 9.6 | 56.8 ± 11 | 14↑ |
| Vit. E | 1238.6 ± 260 | 1979 ± 468 | 61↑ | 1622 ± 311 | 1870 ± 264 | 16↑ |
| Vit. C | 2206 ± 920 | 3009 ± 893 | 42↑ | 2029 ± 445 | 2243 ± 469 | 11↑ |
| Neopt. | 183 ± 71 | 125 ± 36 | 31↓ | 154.5 ± 67 | 147 ± 63 | 9↓ |

Neopt.: Neopterin/Creatinine in the urine

The biochemical data obtained in this study show significant variations of oxidized and reduced species of the thiols in plasma and erythrocytes after food integration with the compositions HOPE A and HOPE B, demonstrating an acceleration of metabolism and an intra- and extra-cellular antioxidant activity.

Administering the HOPE A composition results in a significant increase in erythrocyte glutathione (GSH) levels (equal to 43.7%; $p=10^{-4}$) with a simultaneous decrease in oxidized glutathione (equal to 49%; $p=10^{-5}$). Administering the HOPE B composition leads to a significant increase in erythrocyte GSH levels compared to time t0 ($p=10^{-8}$) but lower (equal to 32.25%) compared to the increase obtained in subjects who took the HOPE A composition.

Administering the HOPE A composition also determines a significant increase in reduced CysGly in the erythrocytes and in the plasma, which is decidedly greater than that observed following administration of the HOPE B composition (polydatin-free). Suffice to say that the percentage increase in reduced CysGly in plasma is equal to 26.5% after administration of the HOPE B composition while it doubles (52.4%) in subjects who took the HOPE A composition. Surprisingly, the percentage increase in reduced CysGly in plasma is equal to 11% after administration of the HOPE B composition while tripling (39%) in subjects who have taken the HOPE A composition.

Another decidedly surprising finding regards evaluating the inflammation marker, neopterin, which decreases by 9% in subjects who have taken the HOPE B composition and by 31% in subjects who have taken the composition comprising polydatin (HOPE A).

The Inventors of this application have also surprisingly observed a widely enhanced effect following the intake of the HOPE A composition on the synthesis of vitamins A, C and E.

This result is of fundamental importance given the antioxidant effect that vitamins A, C, E exert in the body.

Administering the composition including polydatin resulted in a 47% increase in vitamin C levels, 61% of vitamin E levels and 42% vitamin A levels.

Comparing this effect to that obtained following administration of the HOPE B composition, free of polydatin, it is possible to note that the HOPE A composition causes an increase in vitamin C more than four times greater than that induced by the administration of the HOPE B composition (47% versus 11%); a 3.8 times greater increase in vitamin E than that induced by the administration of the HOPE B composition (61% versus 16%); and an increase in vitamin A three times greater than that induced by the administration of the HOPE B composition (42% versus 14%).

These results suggest that glutathione synthesized from its precursors can (through the enzyme dehydroascorbate reductase) regenerate ascorbic acid (vitamin C) from dehydroascorbic acid (DHA), which would otherwise be irreversibly converted to 2,3 diketogulonic acid, with consequent reduction of the levels of vitamin C. Reduction of the levels of dehydroascorbic acid by glutathione represents a very active way that allows the almost total recovery of vitamin C. In turn, vitamin C is able to transform the alpha tocopheroxyl radical into the original form of alpha tocopherol or into vitamin E, neutralizing and eliminating, at the same time, the carotenoid radicals, which can have a pro-oxidant effect if they are not removed from vitamin C.

Furthermore, since vitamin E protects both beta-carotene and vitamin A from oxidation, which are contained within the circulating cells and lipoproteins, an increase in vitamin A levels follows, which is observed following the intake of the HOPE A composition.

The comparative analysis described has, therefore, shown that the activity exercised by the composition comprising polydatin, in combination with precursor amino acids of glutathione and pro-glutathione molecules, such as selenium (Se) causes (compared to the composition comprising the same amino acids but free of polydatin) a greater increase of reduced species of thiols in plasma and erythrocytes and, therefore, of glutathione itself; a greater decrease in oxidized species of thiols in plasma and erythrocytes except for oxidized glutathione; a clearly superior general antioxidant activity; a markedly higher increase in plasma levels of vitamins A, E and C; and a more than three times greater decrease in neopterin, an inflammation marker.

The composition comprising polydatin, in combination with at least one of the indicated amino acids, is therefore able to significantly counteract the damage exerted by oxidative stress. With its antioxidant value, polydatin provides equivalent reduction to the cells and is able to exert its antioxidant activity both directly with the OH group in C4, and indirectly by activating the sirtuins which, in turn, in addition to activating phase II enzymes (antioxidants), increase the activity of two important families of enzymes involving GSH: glutathione-S-Transferase (GST) and glutathione Peroxidase (GPX).

Glutathione-S-transferases (GSTs) are a family of detoxifying isoenzymes that catalyze the conjugation of various toxic molecules with glutathione, making them less reactive and more easily eliminated by the body. This type of conjugation is made possible because GSH contains a reduced sulfur atom SH in the amino acid cysteine that is easily activated to become a powerful nucleophile capable of binding a variety of different molecules, such as electrophilic xenobiotics. These molecules, linked to GSH, become more soluble and can be eliminated. Furthermore, GSH despite being composed of three common amino acids (glutamic acid, cysteine and glycine) differs from normal peptides due to the particular bond between glutamic acid and cysteine; in fact, glutamic acid is not linked to cysteine in the usual way, with the carboxyl in the alpha position, but is linked with the second carboxyl located at the bottom of the side chain—in the gamma position—and this makes GSH a fully recognizable molecule and is not attacked by common peptidases.

Glutathione-S-transferases therefore uses GSH molecules to perform their precious detoxifying "task" and it is in this occasion that the HOPE A composition acts in synergy with the activity of GSTs by synthesizing new molecules, also thanks to the amino acids, precursors of glutathione.

The surprising results observed following administration of the composition including polydatin may be the result of the establishment of a virtuous biochemistry between detoxifying action and renewed glutathione synthesis due to the activity of the polydatin together with amino acid precursors of the glutathione itself.

If the detoxifying activity of GSH is carried out by GSTs, the antioxidant action is the task of GPX, an enzyme belonging to the oxidoreductase class.

There are several isoenzymes encoded by different genes, which vary in cell localization and substrate specificity. Glutathione peroxidase 1 (GPx1) is the most abundant version, present in the cytoplasm of almost all mammalian tissues, which has hydrogen peroxide as its preferred substrate. Glutathione peroxidase 4 (GPx4) has a high preference for lipid hydroperoxides; it is expressed in almost every mammalian cell, albeit at much lower levels. In all cases, the GPX uses GSH as a substrate, and by oxidizing it to disulfide (GSSG), peroxides and peroxyacids are reduced to water and alcohols. Glutathione reductase has the task of returning GSSG to its reduced form (GSH), which is then oxidized again by the GPX to obtain the antioxidant state necessary to achieve cellular homeostasis.

The results of the experimental tests have shown a surprising effect exerted by the different components of the active agent of the composition subject of this description on oxidative stress, inflammation and vitamin synthesis.

Producing the composition is not limited to these examples, but can have variants, which do not exceed the limits of the claims set out below.

Of course, without prejudice to the principle of the invention, the details of construction and the embodiments may vary widely with respect to those described and illustrated purely by way of example, without departing from the scope of the present invention.

The invention claimed is:

1. Antioxidant composition for increasing the levels of vitamins and reducing oxidative damage in a subject, the composition containing an active agent, said active agent consisting of polydatin, acetylcysteine, α-ketoglutaric acid, glutamine, glycine, alanine, and selenium, wherein upon administration to a human subject the antioxidant composition is capable of increasing endogenous vitamin A, vitamin E and vitamin C levels.

2. The antioxidant composition according to claim 1, wherein polydatin is present in an amount less than 15% (weight/weight) of the active agent.

3. The antioxidant composition according to claim 1, wherein acetylcysteine is present in an amount between 25% and 35% (weight/weight) of the active agent.

4. The antioxidant composition according to claim 1, wherein the weight ratio between polydatin and acetylcysteine is between 0.10 and 0.50.

5. The antioxidant composition according to claim 1, wherein glutamine is present in an amount from 10% to 20% (weight/weight) of the active agent.

6. The antioxidant composition according to claim 1, wherein α-ketoglutaric acid is present in an amount from 10% to 20% (weight/weight) of the active agent.

7. The antioxidant composition according to claim 1, wherein glycine is contained in an amount between 10% and 18% (weight/weight) of the active agent.

8. The antioxidant composition according to claim 1, wherein polydatin is present in an amount between 3% and 15% (weight/weight) of the active agent.

9. The antioxidant composition according to claim 3, wherein acetylcysteine is present in an amount between 28% and 32% (weight/weight) of the active agent.

10. The antioxidant composition according to claim 4, wherein the weight ratio between polydatin and acetylcysteine is between 0.15 and 0.30.

11. The antioxidant composition according to claim 5, wherein glutamine is present in an amount between 13% and 18% (weight/weight) of the active agent.

12. The antioxidant composition according to claim 6, wherein α-ketoglutaric acid is present in an amount between 13% and 18% (weight/weight) of the active agent.

13. The antioxidant composition according to claim 7, wherein glycine is contained in an amount between 12% and 16% (weight/weight) of the active agent.

14. The antioxidant composition according to claim 7, wherein the active agent consists of between 3% and 15% (weight/weight) polydatin, between 25% and 35% (weight/weight) acetylcysteine, between 10% and 20% (weight/weight) α-ketoglutaric acid, between 10% and 20% (weight/weight) glutamine, between 10% and 18% (weight/weight) glycine, between 10% and 25% (weight/weight) alanine, and between 0.01% and 0.03% (weight/weight) selenium.

* * * * *